(12) United States Patent
Chang et al.

(10) Patent No.: US 9,919,011 B2
(45) Date of Patent: Mar. 20, 2018

(54) METHOD FOR TREATING AN INFLAMMATORY BRAIN DISEASE COMPRISING ADMINISTERING A STEM CELL-DERIVED EXOSOME

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); So Yoon Ahn, Seoul (KR)

(73) Assignee: SAMSUNG LIFE PUBLIC WELFARE FOUNDATION, Seoul (KR)

(*) Notice: Subject to any disclaimer, the term of this patent is extended or adjusted under 35 U.S.C. 154(b) by 0 days.

(21) Appl. No.: 15/126,053

(22) PCT Filed: Mar. 18, 2015

(86) PCT No.: PCT/KR2015/002640
§ 371 (c)(1),
(2) Date: Sep. 14, 2016

(87) PCT Pub. No.: WO2015/142061
PCT Pub. Date: Sep. 24, 2015

(65) Prior Publication Data
US 2017/0087187 A1    Mar. 30, 2017

(30) Foreign Application Priority Data

Mar. 18, 2014  (KR) ........................ 10-2014-0031624

(51) Int. Cl.
*A61K 35/28* (2015.01)
*A61K 35/545* (2015.01)
*C12N 5/0775* (2010.01)

(52) U.S. Cl.
CPC ............ *A61K 35/28* (2013.01); *A61K 35/545* (2013.01); *C12N 5/0668* (2013.01)

(58) Field of Classification Search
None
See application file for complete search history.

(56) References Cited

U.S. PATENT DOCUMENTS

| | | | | |
|---|---|---|---|---|
| 9,539,285 | B2* | 1/2017 | Chang ..................... | A61K 35/28 |
| 2013/0195899 | A1 | 8/2013 | Ichim et al. ............ | A61K 35/12 |
| 2015/0190429 | A1* | 7/2015 | Beelen ................... | A61K 38/17 424/400 |
| 2016/0310534 | A1* | 10/2016 | Chang ..................... | A61K 35/28 |
| 2016/0333317 | A1* | 11/2016 | Chang ..................... | A61K 35/28 |
| 2017/0121685 | A1* | 5/2017 | De La Rosa .......... | A61K 35/35 |

FOREIGN PATENT DOCUMENTS

| | | | | |
|---|---|---|---|---|
| JP | 2002-535665 | 10/2002 | ............. | G01N 30/88 |
| JP | 2006-509516 | 3/2006 | ................ | C12N 5/06 |
| JP | 2007-521815 | 8/2007 | ......... | A61K 31/7088 |
| JP | 2007-535947 | 12/2007 | ................ | C12N 5/06 |
| KR | 2005-0088118 | 9/2005 | ................ | C12N 5/06 |
| KR | 10-2010-0081003 | 7/2010 | | |
| WO | WO 2012/125471 | 9/2012 | ............. | A61K 35/28 |
| WO | WO 2013/039000 | 3/2013 | ............. | A61K 35/12 |
| WO | WO 2013/102219 | 7/2013 | ............. | C12N 5/073 |
| WO | WO 2013/150303 | 10/2013 | ........... | A61K 31/711 |
| WO | WO 2014/013029 | 1/2014 | | |
| WO | WO 2014/013258 | 1/2014 | ........... | A61K 31/711 |
| WO | WO 2014/013258 A1 * | 1/2014 | | |

OTHER PUBLICATIONS

Mokarizade A. et al. Effect of MSC Derived Exosomes on Polarization of Helper T Cells Responses and Clinical Feature of EAE. Majallah-i Pizishki-i Urumiyah 23(2)220, 191-201, 2012. English translation ordered. (Year: 2012).*
Haney M. et al. Specific Transfection of Inflamed Brain by Macrophages. PLoS One 8(4)1-16, Apr. 19, 2013.*
Denzer K. et al. Exosome: From Internal Vesicle of the Multivesicular Body to Intercellular Signaling Device. J of Cell Science 113: 3365-3374, 2000.*
Kim S. et al. Exosomes From Mouse Bone Marrow Derived Mesenchymal Stem Cells Mediate a Potent Immunosuppressive Function. J of Immunology 186(Suppl 1)167.15, Apr. 1, 2011.*
Verderio C. et al. Myeloid Microvesicles are a Marker and Therapeutic Target for Neuroinflammation. Annals of Neurology 72(4)610-624, Oct. 2012. (Year: 2012).*
Pluchino S. et al. How Stem Cells Speak with Host Immune Cells in Inflammatory Brain Diseases. Glia 61(9)1379-1401, Sep. 2013.*
Fierabracci A. et al. Recent Advances in Mesenchymal Stem Cell Immunomodulation. Cell Transplantation 24:133-149, 2015.*
International Search Report (ISR) dated Jun. 19, 2015 in PCT/KR2015/002640 published as WO 2015/142061 with English Translation.
Kim et al., (2007). "Effective treatment of inflammatory disease models with exosomes derived from dendritic cells genetically modified to express IL-4", *The Journal of Immunology* 179(4):2242-2249.
Xin, H., et al., (2013). "Systematic administration of exosomes released from mesenchymal stromal cells promote functional recovery and neurovascular plasticity after stroke in rats", *Journal of Cerebral Blood Flow & Metabolism* 33:1711-1715.
Extended European Search Report from corresponding European Application No. 14869537.2 dated Apr. 21, 2017.
Extended European Search Report from corresponding European Application No. 14868825.2 dated Jul. 7, 2017.
Office Action from corresponding Japanese Application No. 2016-539061 dated Mar. 21, 2017.

(Continued)

*Primary Examiner* — Ralph J Gitomer
(74) *Attorney, Agent, or Firm* — Harness, Dickey & Pierce, P.L.C.

(57) ABSTRACT

The present invention relates to a composition for treating inflammatory brain diseases, which includes stem cell-derived exosomes as an active ingredient. The stem cell-derived exosomes according to the present invention can be usefully applied to the treatment of inflammatory brain diseases, because the exosomes have outstanding therapeutic effects, including inhibiting cell death due to inflammation in nerve cells, increasing the survival rate in an inflammatory-brain-disease animal model, and substantially reducing brain damage and inflammatory cytokine levels due to inflammatory reactions such as edema.

8 Claims, 9 Drawing Sheets

(56) References Cited

OTHER PUBLICATIONS

Aharon A., et al.; "Microparticles, thrombosis and cancer", 2008 Elsevier Ltd.
Ruenn Chai Lai, et al.; "Mesenchymal stem cell exosome: a novel stem cell-based therapy for cardiovascular disease", Regen. Med., 2011, 6(4), 481-492.
Xin, H. et al.; "System administration of exosomes released from mesnchymal stromal cells promote functional recovery and neurovascular plasticity after stroke in rats", Journal of Cerebral Blood Flow & Metabolism (2013) 33, 1711-1715.
Extended European Search Report from corresponding European Application No. 15764229.9 dated Nov. 10, 2017.
Examination Report dated Sep. 19, 2017 from the Japanese Patent Office—Non-English language.
Lee et al., (2012). "Mouse mesenchymal stem cell-derived exosome mediates a immunosuppressive function in TH17 cells", *The Journal of Immunology 188/Supplement* 1:48.8.
Xin, H., etal., (2012). "Exosome-Mediated Transfer of MiR-133b from Multipotent Mesenchymal Stromal Cells to Neural Cells Contributes to Neurite Outgrowth", *Stem Cells* 30:1556-1564.
Yang et al., (2017). "MCSs-Derived Exosomes and Neuroinflammation, Neurogenesis and Therapy of Traumatic Brain Injury", *Frontiers in Cellular Neuroscience* vol. 11, Article 55.

\* cited by examiner

METHOD FOR TREATING AN INFLAMMATORY BRAIN DISEASE COMPRISING ADMINISTERING A STEM CELL-DERIVED EXOSOME

CROSS-REFERENCE TO RELATED APPLICATIONS

This application is a national phase application of PCT Application No. PCT/KR2015/002640, filed on Mar. 18, 2015, which claims the benefit and priority to Korean Patent Application No. 10-2014-0031624, filed Mar. 18, 2014. The entire disclosures of the applications identified in this paragraph are incorporated herein by references.

FIELD

The present invention relates to a composition for treating inflammatory brain diseases, which includes a stem cell-derived exosome as an active ingredient.

BACKGROUND

Stem cells are undifferentiated cells that have the capacity to differentiate into two or more cell types with self-renewal capacity. Based on differentiation potency, stem cells can be classified into totipotent stem cells, pluripotent stem cells, and multipotent stem cells. Based on biological origin, in addition, stem cells can be classified into embryonic stem cells and adult stem cells. Embryonic stem cells are derived from preimplantation embryos, developing fetal reproductive organs, and the like, whereas adult stem cells are derived from an individual organ, e.g., bone marrow, brain, liver, pancreas, or the like, of adults.

Totipotent stem cells are cells that have the ability to differentiate into any cell in an organism. Totipotency is maintained until the 8-cell stage after fertilization, occurring when a sperm fuses with an egg. Totipotent stem cells can be isolated and then transplanted into the uterus to develop into an intact individual.

Pluripotent stem cells are cells that have the capacity to differentiate into any types of cells and tissues which constitute ectoderm, mesoderm, or endoderm. Stem cells originate from an inner cell mass, located on the inside of a blastocyst that appears 4 to 5 days after fertilization, and the cells are called embryonic stem cells, which have the capacity to differentiate into multiple types of tissue cells, but have no capacity to develop into a new individual.

Multipotent stem cells are stem cells that have the capacity to differentiate only into specialized cell types in a specific tissue and organ where the stem cells are found. Stem cells play a part in functions that maintain adult tissue homeostasis and induce regeneration in the event of tissue damage, as well as growth and development of respective tissue or organs during fetal, neonatal and adult periods. Particularly, adult stem cells are the general term for such tissue-specific multipotent cells. Adult stem cells are derived from existing cells, which are isolated from various organs of the human body and then developed into stem cells. Interestingly, although adult stem cells have general features to differentiate into specialized cell types of the tissue, recent studies have received attention by showing that adult stem cells can differentiate into various tissue cells, such as liver cells.

Stem cells retain characteristics, such as self-renewing, differentiation, immortality, etc. In particular, adult stem cells, which can be obtained from multiple tissues, are widely used in research, because the cells are generally harvested from unlimited sources and avoid the ethical issues with which researchers may be faced when using embryonic stem cells.

Recently, preclinical and clinical research to apply stem cells to various diseases, such as cerebral infarctions, traumatic brain injuries, and musculoskeletal diseases, is underway. However, technologies pertaining to stem cell therapies currently have limitations, only focusing on isolating and culturing/proliferating stem cells, and injection thereof. In addition, recent clinical research results showed that such stem cell therapies do not exhibit distinct effects yet. Accordingly, research using various gene-modified stem cells to increase therapeutic effects is underway. However, application of cell therapy, in which genes are modified, to the human body is limited due to ethical problems.

In addition, there are several problems in applying therapeutic methods using stem cells to clinical trials. For example, tumor masses may be formed after engraftment of stem cells to organs, and cerebral infarction may occur due to an artery occlusion likely induced by the large size of stem cell itself. The stem cells easily move into the brain when the brain-blood vessel barrier is open as in an acute stage. However, in a chronic stage, movement of the stem cells is limited due to large sizes thereof.

Meanwhile, an exosome is a small vesicle with a membrane structure secreted from a variety of cell types. Exosomes reportedly have a diameter of about 30-100 nm. It was observed that exosomes were derived from specific intracellular parts called multivesicular bodies (MVBs) and released and secreted to the outside of cells, instead of being directly detached and released from plasma membranes, by means of an electron microscope. That is, when fusion between multivesicular bodies and plasma membranes occurs, vesicles are released to the outside of cells. These vesicles are called exosomes. Although a molecular mechanism for a formation process of such exosomes is not clearly determined, it is known that a variety of immunocytes including B lymphocytes, T lymphocytes, dendritic cells, platelets, macrophages, etc., tumor cells, and stem cells, as well as red blood cells, produce and secret exosomes during their lifespan. In particular, it is known that, since stem cell-derived exosomes contain nuclear components as well as receptors and proteins, the exosomes play roles in intercellular communication. In addition, since stem cell-derived exosomes contain a relatively small amount of animal serum, compared to stem cells, the risk of symptoms (zoonosis) due to infection caused by animal serum can also be eliminated. Considering such characteristics of exosomes, it is anticipated that cytotherapy using exosomes can be a new paradigm to overcome the limitations of existing stem cell therapies.

Meanwhile, inflammatory brain diseases refer to inflammatory diseases that occur in the brain by specific causes, and the diseases include encephalitis, encephalomeningitis, and meningoencephalitis, etc. Encephalitis is a general term for inflammatory diseases of the cerebral parenchyma and is different from the inflammation (e.g., encephalomeningitis) that occurs in cerebral meninges surrounding the brain. Meningoencephalitis is a medical condition wherein both encephalomeningitis and encephalitis exist simultaneously. Based on cause, encephalitis can be generally classified into infectious, vasculitis, neoplastic, chemical, idiopathic, etc., and further classified depending on the specific causes of disease according to each detailed item. Additionally, encephalitis can be also classified into acute, subacute, and chronic encephalitis depending on the elapsed time of disease. Up to now, antibiotic treatment is used as the method to treat the inflammatory brain diseases. However, although the causative agents of diseases may be eliminated by antibiotic treatment, side effects, including serious brain damage, hydrocephalus, hearing loss, epilepsy, etc., can occur due to use of antibiotics. Thus, development of new therapeutics is required. However, until now, treatments using stem cell-derived exosomes for inflammatory brain diseases have not been systemically studied.

The present inventors have been continuing research on development of a new therapeutic agent for treating inflammatory brain diseases. As a result, the present inventors demonstrated that stem cell-derived exosomes inhibit cell death due to inflammation in nerve cells, and showed that the exosomes have outstanding therapeutic effects in an inflammatory-brain-disease animal model, thus completing the present invention.

DISCLOSURE

Technical Problem

The present invention is directed to providing a pharmaceutical composition for treating inflammatory brain disease, which includes stem cell-derived exosomes as an active ingredient.

Technical Solution

To achieve this purpose, the present invention provides a pharmaceutical composition for treating inflammatory brain diseases, which includes stem cell-derived exosome as an active ingredient.

Advantageous Effects

The stem cell-derived exosomes according to the present invention can be usefully applied to the treatment of inflammatory brain diseases, because the exosomes have outstanding therapeutic effects, including inhibiting cell death due to inflammation in nerve cells, increasing the survival rate in an inflammatory-brain-disease animal model, and substantially reducing brain damage and inflammatory cytokine levels due to inflammatory reactions such as edema.

MODES OF THE INVENTION

Figure 1:
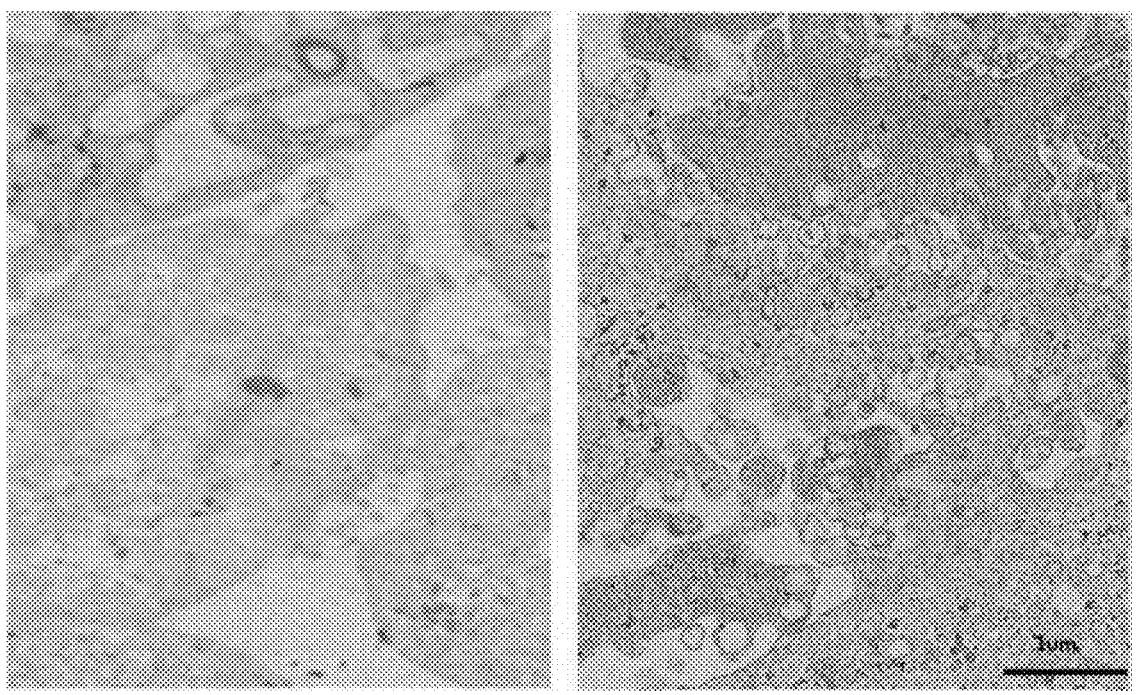
FIG. 1 illustrates the process whereby exosomes are secreted from stem cells treated with thrombin, confirmed by TEM image analysis (left: before thrombin treatment, right: after thrombin treatment).

The present invention provides a pharmaceutical composition for treating inflammatory brain diseases, which includes stem cell-derived exosomes as an active ingredient.

In the present invention, the term "stem cells" refers to undifferentiated cells having the ability to differentiate into two or more different cell types.

The stem cells of the present invention may be autologous or allogeneic stem cells and may be derived from any animal including humans and non-human mammals. In addition, the stem cells may be derived from, without being limited to, adults or embryos.

The stem cells of the present invention include embryonic stem cells or adult stem cells, preferably, adult stem cells. The adult stem cells may be, without being limited to, mesenchymal stem cells, human tissue-derived mesenchymal stromal cells (mesenchymal stromal cell), human tissue-derived mesenchymal stem cells, multipotent stem cells, or amniotic epithelial cells, preferably, mesenchymal stem cells. The mesenchymal stem cells may be derived from, without being limited to, the umbilical cord, umbilical cord blood, bone marrow, fat, muscle, nerve, skin, amnion, placenta, etc.

In the present invention, the term "exosomes" refers to small vesicles having a membrane structure secreted from various cells. Exosomes have diameters of about 30 to 100 nm, and fusion between plasma membranes and multivesicular bodies occurs, thereby being released to the outside of the cells.

In the present invention, inflammatory brain diseases are the general term for all types of inflammatory diseases in the brain, including encephalitis, encephalomeningitis, and meningoencephalitis, preferably encephalomeningitis, more preferably bacterial infection-induced encephalomeningitis.

Encephalomeningitis can be classified into viral and non-viral encephalomeningitis, depending on cause.

Viral encephalomeningitis can be caused by herpes simplex virus, arbovirus, varicella zoster virus, Epstein-Barr virus, cytomegalovirus, and Japanese encephalitis virus, etc., but is not limited thereto.

Non-viral encephalomeningitis can be caused by bacteria (e.g., *haemophilus influenzae, Neisseria encephalitis, Klebsiella pneumonia, streptococcus, staphylococcus, Escherichia coli, streptococcus*, etc.), parasites (e.g., *cysticercus, toxoplasma*), fungi, and protozoa (e.g., amoeba, etc.), etc., without being limited thereto.

In one embodiment, the present inventors confirmed that stem cell-derived exosomes have outstanding therapeutic effects, including inhibiting cell death due to inflammation in nerve cells, increasing the survival rate in an inflammatory-brain-disease animal model, and substantially reducing brain damage and inflammatory cytokine levels due to inflammatory reactions such as edema.

Accordingly, the stem cell-derived exosomes according to the present invention can be usefully used as therapeutic agents for the treatment of inflammatory brain diseases.

A composition of the present invention may further include one or more publicly known active ingredients, having therapeutic effects on inflammatory brain diseases, along with the stem cell-derived exosomes.

A composition of the present invention may further include the internal contents of exosomes along with the stem cell-derived exosomes.

The internal contents of exosomes include proteins, lipids, mRNAs, and microRNAs, etc., without being limited thereto, which are derived from tissues or cells that are sources of the exosomes.

A composition of the present invention may further include appropriate carriers, generally used to prepare pharmaceutical compositions. For example, a formulation for injection may further include preservatives, agents for relieving pain upon injection, solubilizers, stabilizers, etc., and a formulation for topical administration may further include bases, vehicles, lubricants, preservatives, etc.

The composition of the present invention may be formulated into a medicine having a unit dosage form suitable for being administered into the body of a subject according to a general method used in the pharmaceutical field. As preferred examples of formulations for parenteral administration suitable for accomplishing such a purpose, there are injection agents such as an ampule for injection, infusion agents such as an infusion bag, spraying agent such as an aerosol formulation, and the like. The ampule for injection may be mixed with an injectable solution immediately before use. The injectable solution may be a saline solution, glucose, Ringer's solution, or the like. In addition, the infusion bag may be made of polyvinyl chloride or polyethylene. In the present invention, the administration indicates that an individual is provided with the prescribed composition of the present invention through any appropriate methods.

The pharmaceutical composition of the present invention may be administered to an individual through various paths. All methods for administration could be anticipated. For example, the composition may be administered by oral, rectal, intravascular (such as intravenous, intra-arterial, etc.), intramuscular, subcutaneous, intrauterine, or cerebrovascular injection. Preferably, the composition may be directly engrafted or transplanted into the cerebral ventricle of an individual requiring treatment, but the present invention is not limited thereto.

A preferable dosage of the pharmaceutical composition of the present invention depends on conditions and weights of individuals, progression of diseases, drug types, administration paths and administration periods, which may be appropriately selected by those of ordinary skill in the art. The composition may be administered once a day, or several times separately, without being limited thereto.

For treatment of inflammatory brain diseases, the composition of the present invention may be used alone or in combination with methods such as surgery, radiation therapy, hormone therapy, chemical therapy, and regulators of biological reactions.

Hereinafter, the present invention will be described in more detail with reference to the following preferred examples. However, it should be understood that the following examples serve merely to concretely explain the spirit of the invention and therefore, there is no intent to limit the invention to the examples.

Example 1. Isolation of Stem Cell-Derived Exosomes

To isolate stem cell-derived exosomes, an ultracentrifuge was used. More specifically, human umbilical cord blood-derived mesenchymal stem cells, diluted in culture media at a concentration of $1 \times 10^5$ cells/ml, were aliquoted into 60 mm culture dishes (3 ml/dish) and then cultured for one week. After confirming that the surface of the culture dish was entirely covered with the cultured stem cells, the culture medium thereof was replaced with a new culture medium containing thrombin at a concentration of 50 U/ml and then the stem cells were further cultured for 24 hours. After that, the culture medium was aliquoted into 2 ml centrifuge tubes and then centrifuged at 4° C. and 10000 g for 30 minutes, followed by removal of cell debris by transferring the supernatants to a new tube. The supernatants were again ultracentrifuged at 4° C. and 100,000 g for two hours, and the subsequent supernatants was removed to isolate exosomes (at a final concentration of 15 mg/ml).

The process of exosome secretion from stem cells was confirmed by TEM image analysis. The exosomes were isolated using the methods described above, and then the expression levels of exosome markers, CD63 and CD9 (System Bioscience, Mountain View, Calif., USA), were assessed by western blotting, as illustrated in the FIG. 1 and FIG. 2.

As illustrated in the FIG. 1, it was confirmed that thrombin treatment promotes exosome secretion from mesenchymal stem cells.

Figure 2:
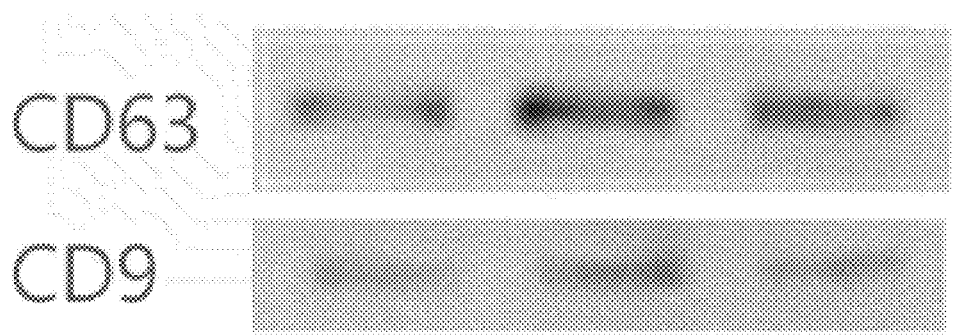
FIG. 2 illustrates whether exosome markers, CD63 and CD9, are normally expressed in stem cell-derived exosomes that are isolated according to the present invention.

Additionally, as illustrated in FIG. 2, it was confirmed that the isolated stem cell-derived exosomes normally express exosome markers such as CD63 and CD9.

Example 2. In Vitro Investigation into the Protective Effects of Stem Cell-Derived Exosomes on Nerve Cells To investigate the protective effects of stem cell-derived exosomes, obtained according to Example 1, on nerve cells, the following experiments were performed.

First, rats were sacrificed at 18.5 days' gestation to obtain fetuses, and then the cerebral cortexes of the fetuses were isolated, followed by culture with primary glial cells and nerve cells for 7 days. Cell death was observed in the cells, which were treated with LPS (lipopolysaccharides) at different concentrations, as illustrated in the FIG. 3.

Figure 3:
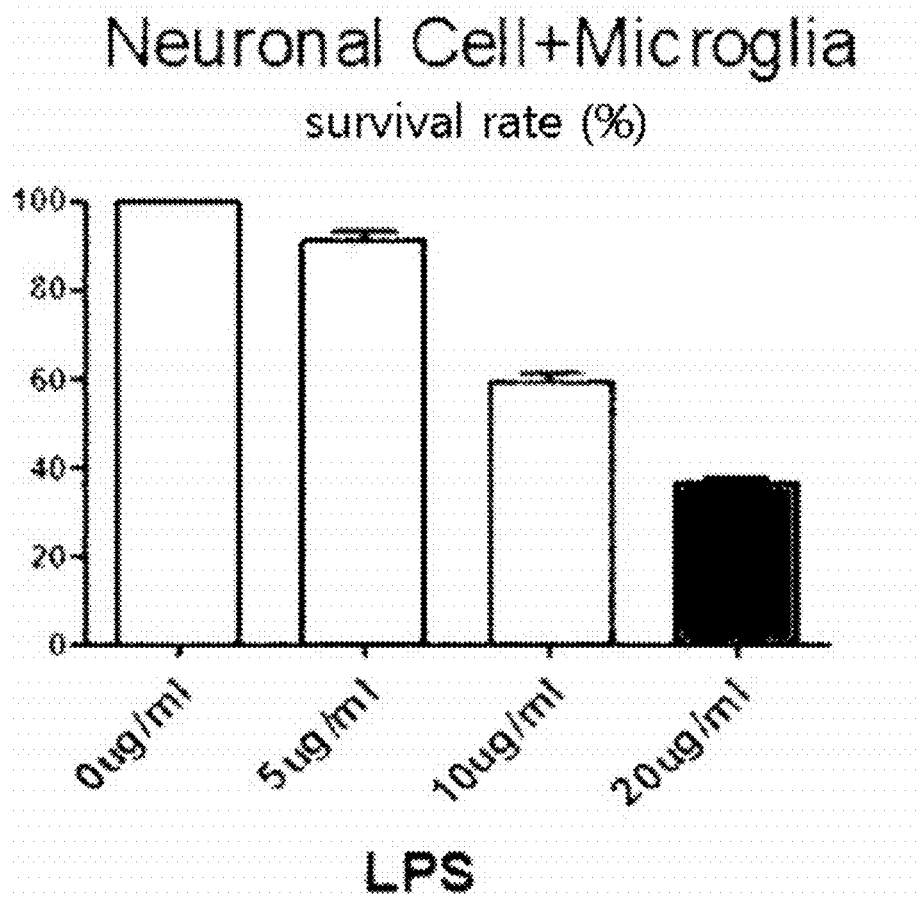
FIG. 3 illustrates the viability of nerve cells depending on the concentration of LPS, when nerve cells are treated with thrombin.

As illustrated in the FIG. 3, it was confirmed that about 40% of nerve cells die when exposed to LPS at a concentration of 10 µg/ml. Thereafter, the nerve cells treated with LPS at the concentration were used as a brain inflammatory cell model.

Figure 4:
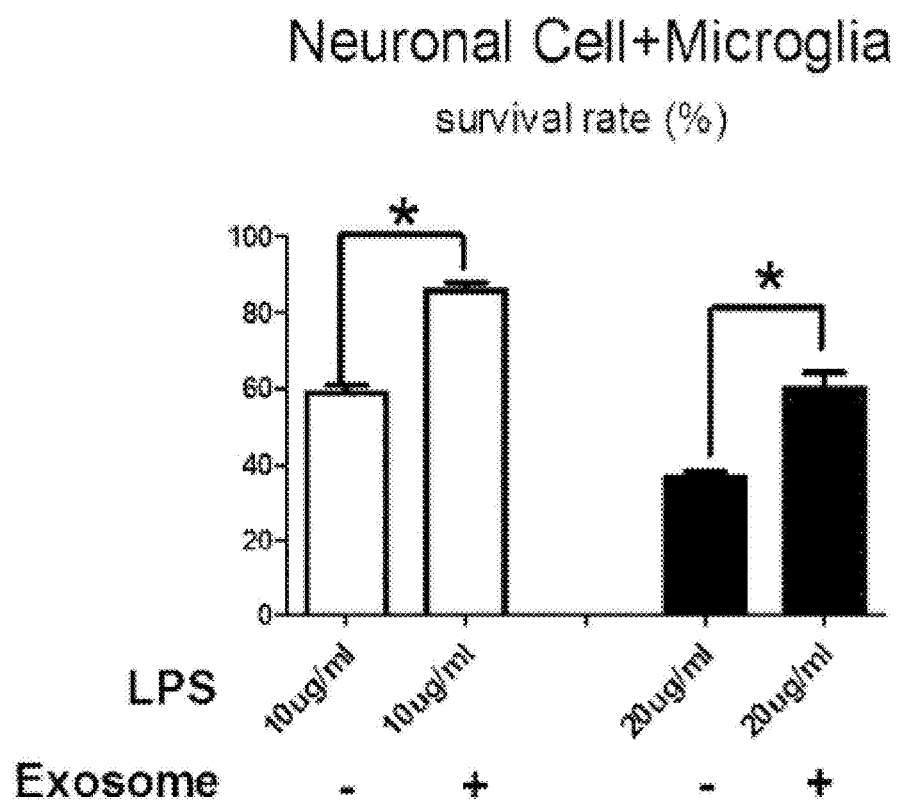
FIG. 4 illustrates the viability of nerve cells treated with LPS and then with stem cell-derived exosomes according to the present invention.

Next, the nerve cells, treated with LPS at the concentration of 10 µg/ml, were treated with 15 µg of the stem cell-derived exosomes, obtained according to Example 1, and then cell survival rates were assessed using a cell count kit (Dojindo, Kumamoto, Japan), as illustrated in FIG. 4.

As illustrated in FIG. 4, it was confirmed that cell death rates are substantially suppressed when the cell death-induced nerve cells are treated with stem cell-derived exosomes according to the present invention, thus confirming the protective effects of stem cell-derived exosomes on nerve cells.

Example 3. In Vivo Investigation into the Therapeutic Effects of Stem Cell-Derived Exosomes on Inflammatory Brain Diseases 3-1. Design of Bacterial Infection-Induced Encephalomeningitis Animal Model To generate a bacterial infection-induced encephalomeningitis animal model, newborn rats at 10 days after birth were subjected to inhalation anesthesia, and the right cerebral ventricles of the rats were slowly administered *E. coli* (*Escherichia coli*) (10 μl) of $1 \times 10^3$ CFU (colony forming unit) using a stereotaxic frame with 31 gauge syringe for 60 seconds, followed by administration of antibiotics (ampicillin, 200 mg/kg) every 12 hours for 2 days. To confirm the therapeutic effects of stem cell-derived exosomes according to the present invention on encephalomeningitis, the mesenchymal stem cell-derived exosomes (20 μg), obtained according to Example 1, were diluted with 10 μl PBS, and then the diluted exosomes were slowly administered into the right cerebral ventricles of the rats (MEN+MSC exosome) in an experimental group, using a stereotaxic frame, under nitrogen monoxide (NO) inhalation anesthesia at 11 days (P11), the day after modeling (bacterial infection-induced encephalomeningitis). In the case of the control group (MEN), physiological saline was administered into the right cerebral ventricles of rats, while the same amount of fibroblast-derived exosomes was administered into the right cerebral ventricles of rats in the comparison group (MEN+fibroblast).

3-2. Analysis of Survival Rates and Brain Tissues

Survival rates were analyzed during experiment period, and brain weights were measured and the regions of damaged brains were analyzed by MRI scan after the experiment.

More specifically, at 6 days after inducing encephalomeningitis by bacterial infection, each limb of a rat was fixed, and the thorax of the rat was opened by incision to expose the heart and lung tissues, and the right ventricle was punctured at a state at which a 23 gauge needle was fixed within the left ventricle, and then 4% paraformaldehyde was allowed to flow through the right ventricle puncture. Thereafter, brain tissues were carefully removed and weighed. Additionally, the brains of rats were monitored using 7-Tesla magnetic resonance imaging (MRI) at 1 day and 6 days after inducing encephalomeningitis, and the degree of brain damage by encephalomeningitis was assessed with DWI (Diffusion Weighted Image) regions. By analysis of brain MRI images using the Image J program, expansion of the cerebral ventricle and cerebral parenchyma infarction region of DWI was assessed and determined as brain damage, and then the ratios of "damaged volume/whole volume of brains" were obtained. The experiment results are shown in the FIGS. 5 to 7, respectively.

Figure 5:
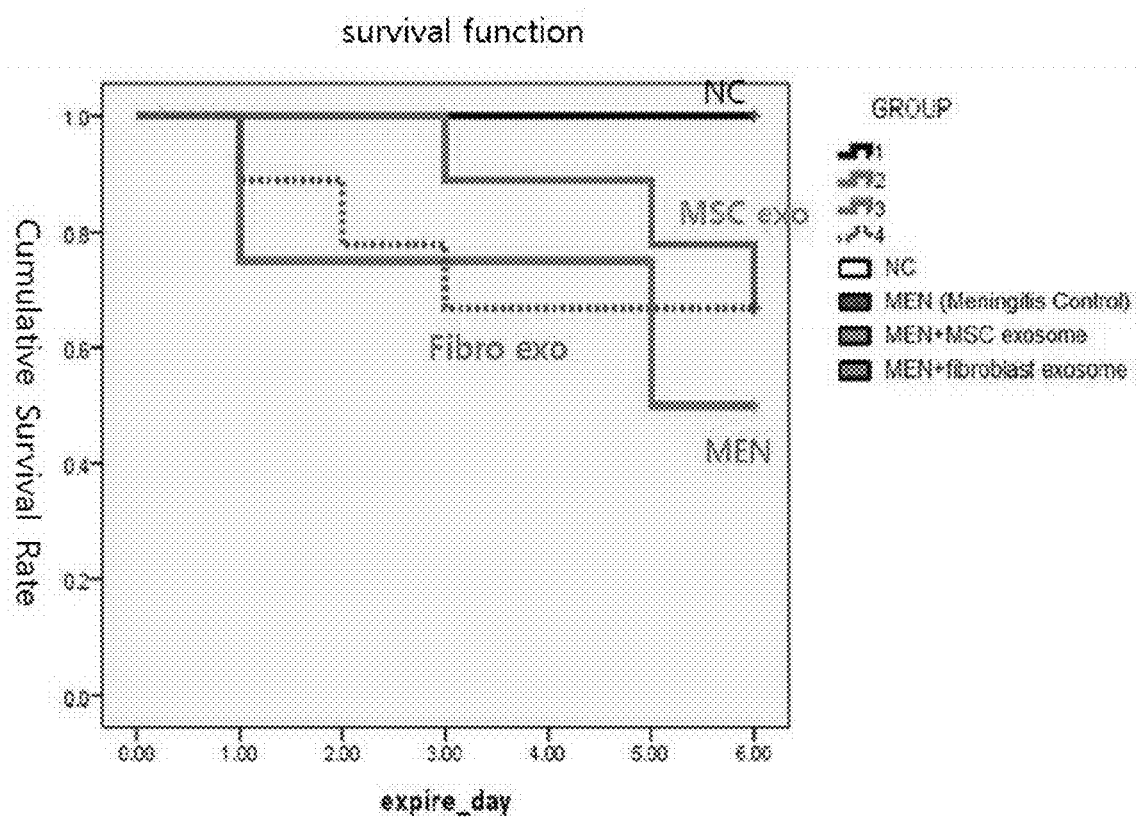
FIG. 5 illustrates the survival rate during the experiment period using an inflammatory-brain-disease animal model.

As illustrated in FIG. 5, it was confirmed that the experimental group (MEN+MSC exosome), administered with mesenchymal stem cell-derived exosomes, exhibited higher survival rates, compared to the control (MEN) and comparison (MEN+fibroblast) groups with encephalomeningitis.

Figure 6:
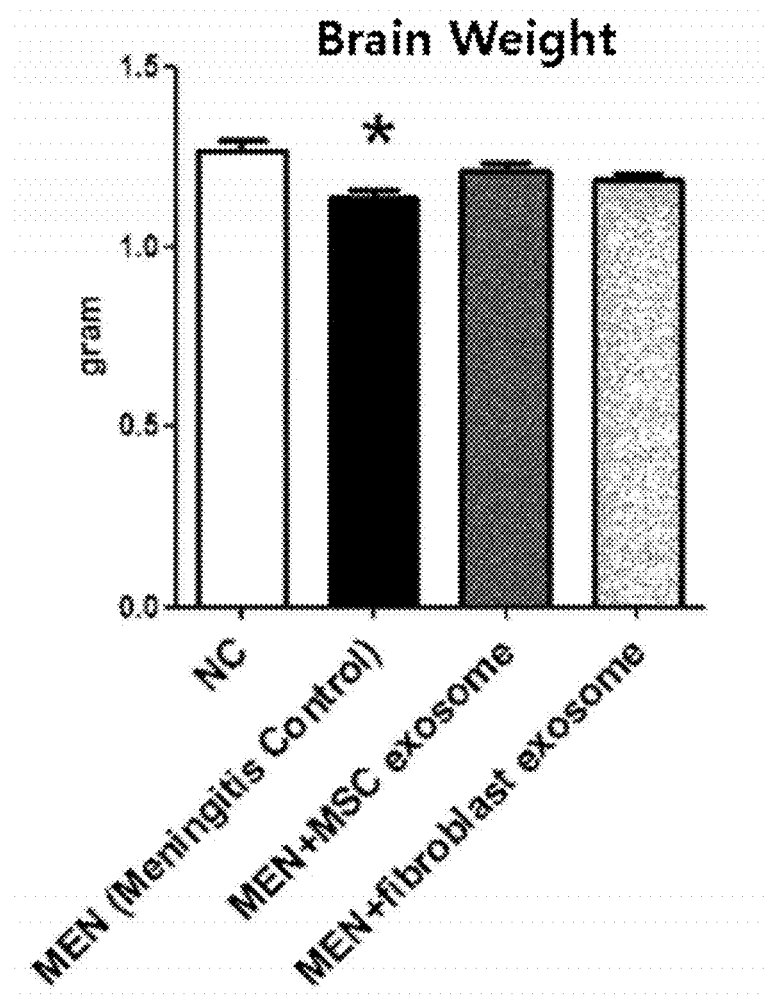
FIG. 6 illustrates results of measuring brain weights after the experiment using an inflammatory-brain-disease animal model.

Additionally, as illustrated in FIG. 6, it was confirmed that the brain weight of the control (MEN) group is significantly decreased, compared to that of the normal (NC) group, whereas the brain weight of the experimental group (MEN+MSC exosome), administered with mesenchymal stem cell-derived exosomes, is not different from that of the normal (NC) group.

Figure 7:
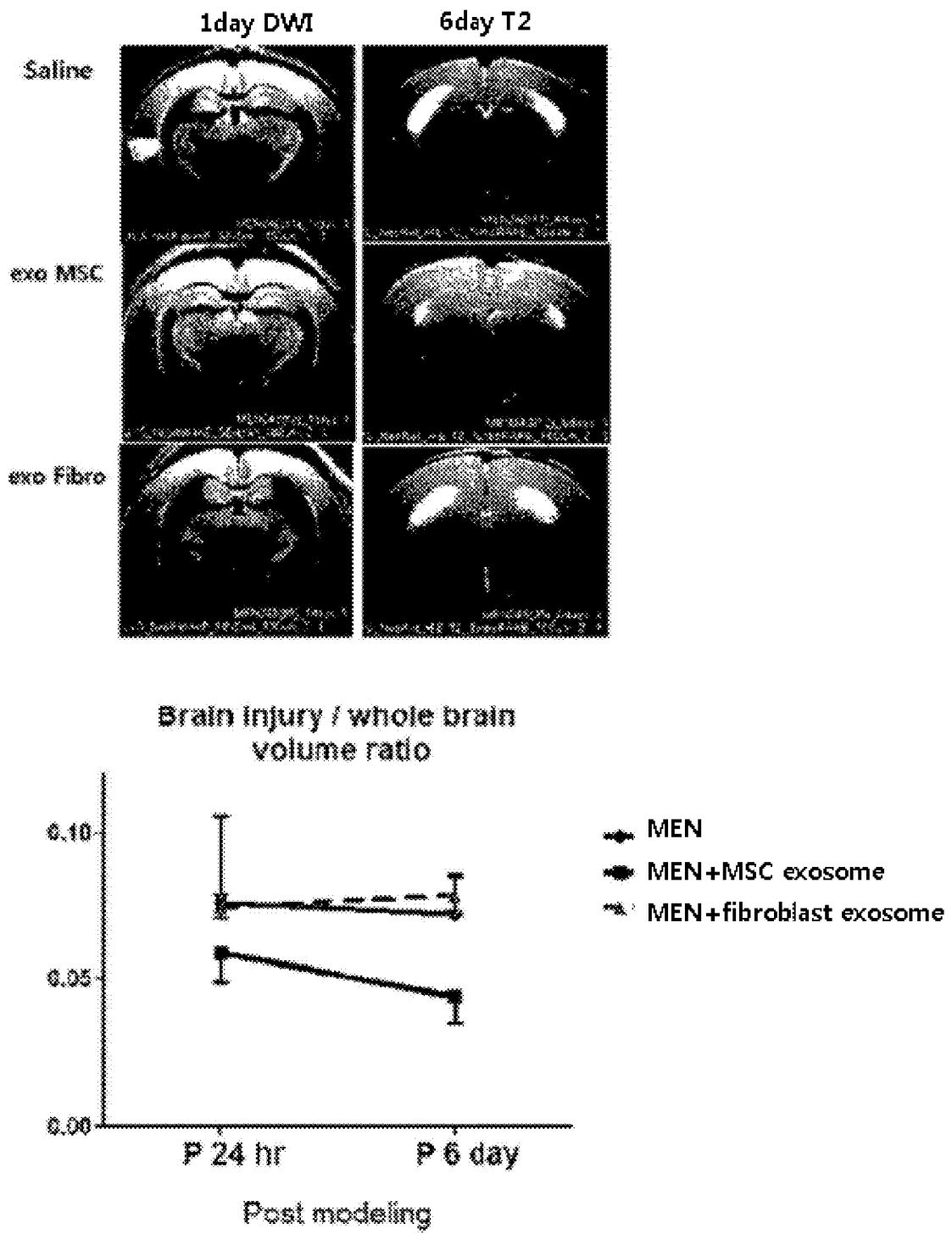
FIG. 7 illustrates the results of MRI brain scans and changes in the ratios of damaged areas/whole areas of brains at 1 day and 6 days after inducing inflammatory brain disease.

Additionally, as illustrated in FIG. 7, it was confirmed that the encephalomeningitis control (MEN, Saline) group shows signs of cerebral parenchymal edema and ventricular dilation and exhibits brain damage, whereas the experimental (MEN+MSC exosome) group, administered with mesenchymal stem cell-derived exosomes, exhibits significant improvement of brain damage, compared to the control (MEN) and comparison (MEN+fibroblast) groups with encephalomeningitis during the experiment period.

3-3. Analysis of Protein Expression in Brain Tissues

Figure 8:
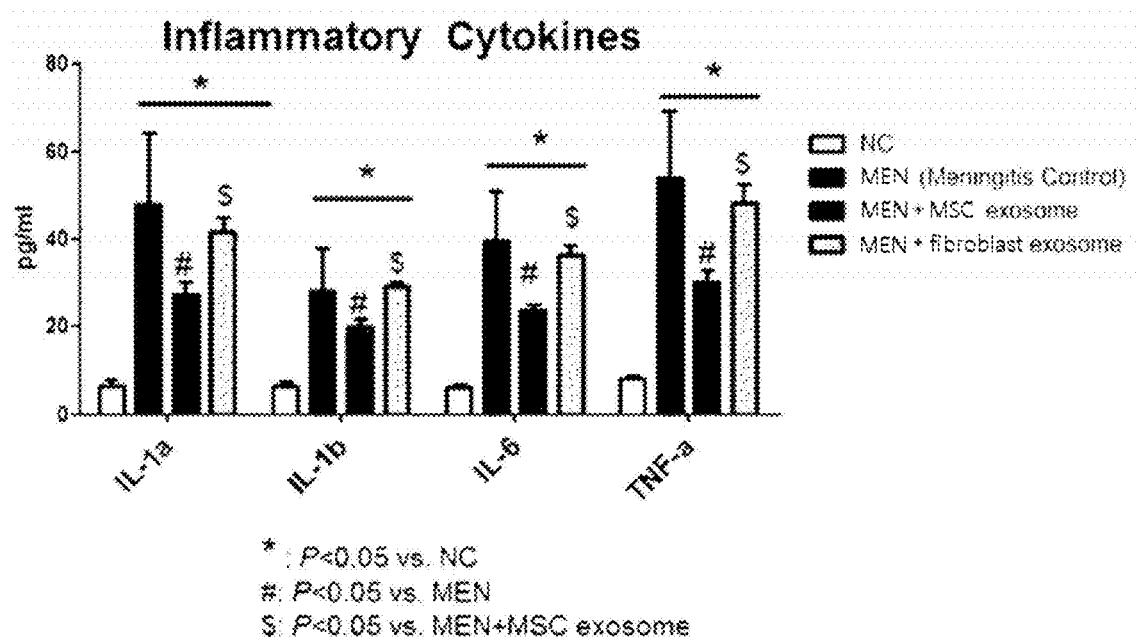
FIG. 8 illustrates the expression levels of inflammatory cytokines within brain tissues in inflammatory-brain-disease animal models, depending on whether stem cell-derived exosomes are administered.
Figure 9:
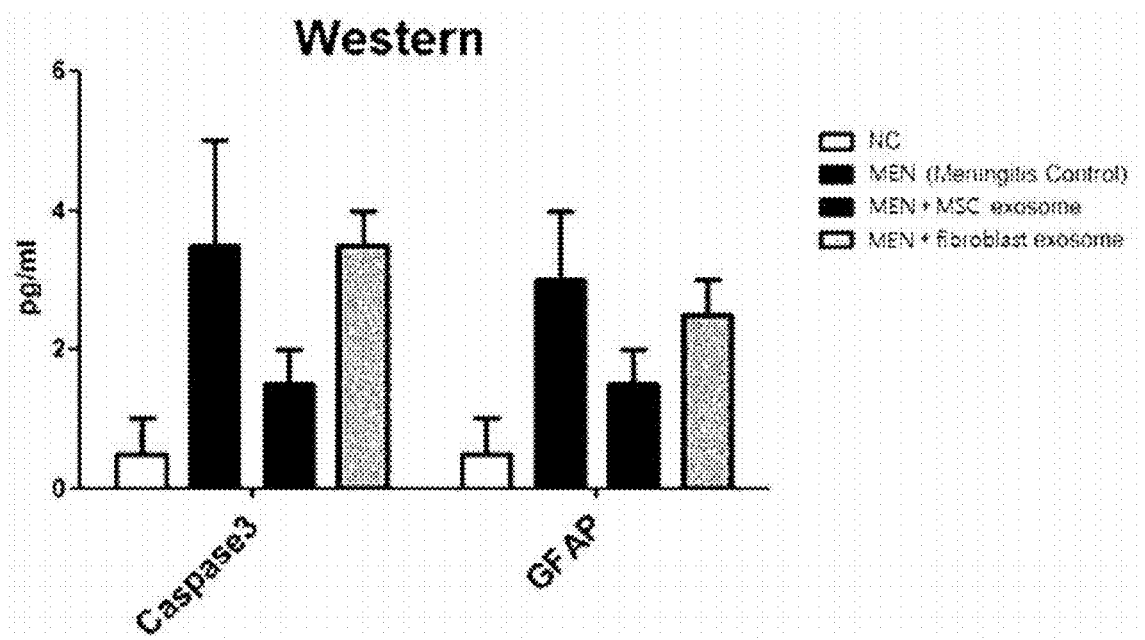
FIG. 9 illustrates the expression levels of proteins within brain tissues in inflammatory-brain-disease animal models, depending on whether stem cell-derived exosomes are administered.

After proteins were isolated from brain tissues, obtained according to Example 3-2, the expression levels of inflammatory cytokines (IL-1α, IL-1β, IL-6, and TNF-α) were assessed by the publicly known ELISA (enzyme-linked immunosorbent assay) method, and the expression levels of caspase-3 and GFAP were assessed by western blotting, as illustrated in FIGS. 8 and 9, respectively.

As illustrated in FIG. 8, the values of inflammatory cytokines in the brains were highly increased in the encephalomeningitis control (MEN) group, compared to the normal (NC) group. Whereas the cytokine values of the experimental (MEN+MSC exosome) group, administered with mesenchymal stem cell-derived exosomes, were significantly improved, compared to the encephalomeningitis control (MEN) group, also exhibited outstanding results in comparison with the comparison (MEN+fibroblast) group.

Additionally, as illustrated in FIG. 9, the expression levels of caspase-3 and GFAP, by which the degree of reactive gelation and cell death can be determined, were markedly increased in the encephalomeningitis control (MEN) group, compared to the normal (NC) group. These results confirmed that brain damage occurred in the control (MEN) group. Whereas the experimental (MEN+MSC exosome) group, administered mesenchymal stem cell-derived exosomes, exhibited significant reduction in the expression levels of caspase-3 and GFAP, compared to the encephalomeningitis control (MEN) group, also exhibited outstanding results in comparison with the comparison (MEN+fibroblast) group.

Through the experimental results, it was confirmed that the present invention has outstanding therapeutic effects on inflammatory brain diseases, including inhibiting cell death due to inflammation in nerve cells, increasing the survival rate in an inflammatory-brain-disease animal model, and substantially reducing brain damage and inflammatory cytokine levels due to inflammatory reactions such as edema.

What is claimed is:

1. A method for treating an inflammatory brain disease, comprising:
    administering to a subject in need thereof an effective amount of exosome derived from a stem cell,
       wherein the inflammatory brain disease is selected from the group consisting of encephalitis, encephalomeningitis, and meningoencephalitis, and
       wherein the stem cell is a mesenchymal stem cell.

2. The method according to claim 1, wherein the mesenchymal stem cell is derived from one or more tissues selected from the group consisting of umbilical cord, cord blood, bone marrow, fat, muscle, nerve, skin, amnion, and placenta.

3. The method according to claim 1, wherein the encephalomeningitis is induced by one or more infectious agents selected from the group consisting of bacteria, parasites, fungi, protozoa, and viruses.

4. The method according to claim 3, wherein the encephalomeningitis is bacterial infection-induced encephalomeningitis.

5. The method according to claim 1, wherein the composition further comprises the internal contents of exosomes in addition to exosomes.

6. The method according to claim 1, wherein the composition is administered orally, rectally, intravascularly, intramuscularly, subcutaneously, intrauterinely, cerebrovascularly, or intraventricularly.

7. The method according to claim 1, wherein the stem cell is treated with thrombin.

8. The method according to claim 1, wherein the exosome is administered in a pharmaceutical composition containing a pharmaceutically acceptable carrier.

* * * * *